United States Patent [19]
Grosvenor et al.

[11] Patent Number: 4,833,166
[45] Date of Patent: May 23, 1989

[54] GROWTH HORMONE RELEASING HORMONE COMPLEMENTARY PEPTIDES

[76] Inventors: Clark E. Grosvenor, 11081 Shady La., Eads, Tenn. 38028; Balint Kacsoh, 550 Techno La., No. 606, Memphis, Tenn. 38105

[21] Appl. No.: 45,687

[22] Filed: May 1, 1987

[51] Int. Cl.[4] .............. A61K 37/43; C07K 7/10; C07K 7/08
[52] U.S. Cl. ................................. 514/12; 514/14; 530/324; 530/327
[58] Field of Search .......... 530/324, 325, 327, 387; 514/14; 424/85

[56] References Cited
PUBLICATIONS

Chem. Abstr., vol. 102, (1985), 110758, 216310.
Chem. Abstr., vol. 103, (1985), 116676.

Primary Examiner—Delbert R. Phillips
Attorney, Agent, or Firm—George W. Neuner; Linda M. Buckley

[57] ABSTRACT

The present invention provides synthetic peptides and fragments and analogs thereof complementary to growth hormone releasing hormone, and antibodies raised against such peptides. The present invention also includes methods of using such peptides and antibodies.

5 Claims, 11 Drawing Sheets

| | | | | | | | | | | |
|---|---|---|---|---|---|---|---|---|---|---|
| GHRH | N-t | His | Ala | Asp | Ala | Ile | Phe | Thr | Ser | Ser | Tyr |
| +RNA | 5' | CAU | GCA | GAC | GCC | AUC | UUC | ACC | AGC | AGC | UAC |
| −RNA | 3' | GUA | CGU | CUG | CGG | UAG | AAG | UGG | UCG | UCG | AUG |
| 3'→5' CP | N-t | Val | Arg | Leu | Arg | STOP | Lys | Trp | Ser | Ser | Met |
| 5'→3' CP | C-t | Met | Cys | Val | Gly | Asp | Glu | Gly | Ala | Ala | Val |
| | | | | | | | | | | | |
| GHRH | | Arg | Arg | Ile | Leu | Gly | Gln | Leu | Tyr | Ala | Arg |
| +RNA | | CGG | AGA | AUC | CUG | GGC | CAA | UUA | UAU | GCC | CGC |
| −RNA | | GCC | UCU | UAG | GAC | CCG | GUU | AAU | AUA | CGG | GCG |
| 3'→5' CP | | Ala | Ser | STOP | Asp | Pro | Val | Asn | Ile | Arg | Ala |
| 5'→3' CP | | Pro | Ser | Asp | Gln | Ala | Leu | STOP | Ile | Gly | Ala |
| | | | | | | | | | | | |
| GHRH | | Lys | Leu | Leu | His | Glu | Ile | Met | Asn | Arg | Gln |
| +RNA | | AAA | CUG | CUG | CAC | GAA | AUC | AUG | AAC | AGG | CAG |
| −RNA | | UUU | GAC | GAC | GUG | CUU | UAG | UAC | UUG | UCC | GUC |
| 3'→5' CP | | Phe | Asp | Asp | Val | Leu | STOP | Tyr | Leu | Ser | Val |
| 5'→3' CP | | Phe | Gln | Gln | Val | Phe | Asp | His | Val | Pro | Leu |
| | | | | | | | | | | | |
| GHRH | | Gln | Gly | Glu | Arg | Asn | Glu | Glu | Gln | Arg | Ser |
| +RNA | | CAA | GGG | GAG | AGG | AAC | CAG | GAA | CAA | AGA | UCC |
| −RNA | | GUU | CCC | CUC | UCC | UUG | GUC | CUU | GUU | UCU | AGG |
| 3'→5' CP | | Val | Pro | Leu | Ser | Leu | Val | Leu | Val | Ser | Arg |
| 5'→3' CP | | Leu | Pro | Leu | Pro | Val | Leu | Phe | Leu | Ser | Gly |
| | | | | | | | | | | | |
| GHRM | | Arg | Phe | Asn | C-t | | | | | | |
| +RNA | | AGG | UUC | AAC | 3' | | | | | | |
| −RNA | | UCC | AAG | UUG | 5' | | | | | | |
| 3'→5' CP | | Ser | Lys | Leu | C-t | | | | | | |
| 5'→3' CP | | Pro | Glu | Val | N-t | | | | | | |

| | | | | | | | | | | |
|---|---|---|---|---|---|---|---|---|---|---|
| GHRH | N-t | His | Ala | Asp | Ala | Ile | Phe | Thr | Ser | Ser | Tyr |
| +RNA | 5' | CAU | GCA | GAC | GCC | AUC | UUC | ACC | AGC | AGC | UAC |
| −RNA | 3' | GUA | CGU | CUG | CGG | UAG | AAG | UGG | UCG | UCG | AUG |
| 3'→5' CP | N-t | Val | Arg | Leu | Arg | STOP | Lys | Trp | Ser | Ser | Met |
| 5'→3' CP | C-t | Met | Cys | Val | Gly | Asp | Glu | Gly | Ala | Ala | Val |
| GHRH | | Arg | Arg | Ile | Leu | Gly | Gln | Leu | Tyr | Ala | Arg |
| +RNA | | CGG | AGA | AUC | CUG | GGC | CAA | UUA | UAU | GCC | CGC |
| −RNA | | GCC | UCU | UAG | GAC | CCG | GUU | AAU | AUA | CGG | GCG |
| 3'→5' CP | | Ala | Ser | STOP | Asp | Pro | Val | Asn | Ile | Arg | Ala |
| 5'→3' CP | | Pro | Ser | Asp | Gln | Ala | Leu | STOP | Ile | Gly | Ala |
| GHRH | | Lys | Leu | Leu | His | Glu | Ile | Met | Asn | Arg | Gln |
| +RNA | | AAA | CUG | CUG | CAC | GAA | AUC | AUG | AAC | AGG | CAG |
| −RNA | | UUU | GAC | GAC | GUG | CUU | UAG | UAC | UUG | UCC | GUC |
| 3'→5' CP | | Phe | Asp | Asp | Val | Leu | STOP | Tyr | Leu | Ser | Val |
| 5'→3' CP | | Phe | Gln | Gln | Val | Phe | Asp | His | Val | Pro | Leu |
| GHRH | | Gln | Gly | Glu | Arg | Asn | Glu | Glu | Gln | Arg | Ser |
| +RNA | | CAA | GGG | GAG | AGG | AAC | CAG | GAA | CAA | AGA | UCC |
| −RNA | | GUU | CCC | CUC | UCC | UUG | GUC | CUU | GUU | UCU | AGG |
| 3'→5' CP | | Val | Pro | Leu | Ser | Leu | Val | Leu | Val | Ser | Arg |
| 5'→3' CP | | Leu | Pro | Leu | Pro | Val | Leu | Phe | Leu | Ser | Gly |
| GHRM | | Arg | Phe | Asn | C-t | | | | | | |
| +RNA | | AGG | UUC | AAC | 3' | | | | | | |
| −RNA | | UCC | AAG | UUG | 5' | | | | | | |
| 3'→5' CP | | Ser | Lys | Leu | C-t | | | | | | |
| 5'→3' CP | | Pro | Glu | Val | N-t | | | | | | |

FIG. 1A

| | Hydrophobic | | Hydrophilic | | Hydrophobic | |
|---|---|---|---|---|---|---|
| hGHRH | 22-Leu | 23-Leu | 24-Gln | 25-Asp | 26-Ile | 27-Met |
| rat GHRH | 22-Leu | 23-Leu | 24-His | 25-Glu | 26-Ile | 27-Met |
| 3'-5' CP | 20-Ala | 21-Phe | 22-Asp | 23-Asp | 24-Val | 25-Leu |
| 5'-3' CP | 24-Ala | 23-Phe | 22-Gln | 21-Gln | 20-Val | 19-Phe |

FIG. 1B

SPECIFICITY OF DOSE — RESPONSE OF PURIFIED IgG MOLECULES

GROWTH HORMONE RELEASING HORMONE COMPLEMENTARY PEPTIDES

This invention was made with Government support under grants HD-20074 and HD-04358, awarded by the National Institutes of Health. The Government has certain rights in this invention.

BACKGROUND OF THE INVENTION

This invention relates to biologically important synthetic Growth Hormone Releasing Hormone complementary peptides and antibodies thereto.

Growth Hormone Releasing Hormone (GHRH), also known as Growth Hormone Releasing Factor, is a hypothalamic peptide which positively regulates the synthesis and secretion of growth hormone in the anterior pituitary. GHRH was originally isolated and structurally characterized from human pancreatic tumors that caused acromegaly. Since then, GHRH has been isolated from several different species, including rat, pig, cow, man, sheep, and goat (Bohlen et al., *Biochem. Biophys. Res. Comm.* 125: 1005–1012, 1984).

GHRH has been widely studied. The amino acid sequence of rat hypothalamic GHRH has been determined (Bohlen et al., 1984, supra). Also, the cDNA to rat GHRH has been reported (Mayo et al., *Nature* 314: 464–467, 1985). Human GHRH is reported to have high homology with rat GHRH and a GH-stimulating effect on the rat pituitary gland (Baird et al., *Neuroendocrinology* 42: 273–276, 1986). Ling et al., *Biochem. Biophys. Res. Comm.* 123: 854–861, (1984) tested the capacity of a series of C-terminal deleted analogs of synthetic human GHRH to release growth hormone and report that the minimal biologically important core of GHRH with full intrinsic activity comprises the fragment (3-21).

Biro suggested (Biro, *Medical Hypotheses,* 7:969–1007, 1981) that protein-protein interactions are based on binding of restricted portions of the proteins that are primarily formed by "informational complementary (ic)" amino acids. He also suggested that these specific complementary amino acids are encoded by complementary DNA sequences; further, interaction between complementary amino acid sequences would occur both in parallel and in antiparallel alignment of the peptides. Although Biro (1981) investigated only the 5'-3' direction, his data also support the significance of the 3'-5' direction by emphasizing the importance of palindrome nucleic acid sequences in encoding the specifically interacting peptide sequences.

Model peptides designed to have minimal homology to the naturally occurring peptide but having the same hydropathic pattern have been demonstrated to exhibit biological activity (See, e.g., Kaiser and Kezdy, *Science,* 223: 249–255, 1984). Blalock and Smith reported that codons for hydrophilic and hydrophobic amino acids on one strand of DNA are complemented by codons for hydrophobic and hydrophilic amino acids on the other DNA strand, respectively, and that codons for slightly hydrophilic ("uncharged") amino acids are complemented by codons for amino acids of the same character (*Biochem. Biophys. Res. Comm.* 121: 203–207, 1984). These workers theorize that the two complementary strands of the DNA encode two peptides having hydropathic anti-complementarity. It has been reported that the hydropathic anti-complementarity of a number of amino acids (and hence that of the peptides) based on the genetic code occurs when complementary codons are read in the 5'-3' as well as in the 3'-5' direction (Bost et al., *Proc. Natl. Acad. Sci.* 82: 1372–1375, 1985a; Bost et al., *Biochem. Biophys. Res. Comm.* 128: 1372–1380, 1985b; Blalock and Bost, *Biochem. J.* 234: 679–683, 1986).

Bost et al., 1985a, supra, have reported that a peptide ("HTCA") corresponding to the complementary (5'-3') RNA sequence of ACTH (1-24) mRNA is capable of binding synthetic ACTH as determined by ELISA. Blalock and Bost, supra, have reported that both 3'-5' and 5'-3' complementary peptides bind $^{125}$I-ACTH in a solid phase binding assay. Similar binding was reported for 5'-3' complementary peptides of γ-endorphin (Bost et al., 1985a, supra). Antibodies raised against the complementary peptide, HTCA, have been reported to stimulate corticosterone secretion of adrenocortical cells in vitro (Bost et al., 1985a, supra). It is also reported that, using the same antibodies in immune affinity chromatography, the ACTH-receptor was purified and its molecular structure and $^{125}$I-ACTH binding characteristics were determined (Bost and Blalock, *Molec. Cell. Endocrinol.* 44: 1–9, 1986). According to Bost et al., 1985b, supra, messenger RNA sequences complementary to the mRNA sequences for the receptors of epidermal growth factor (EGF), interleukin-2 (IL-2) and transferrin (TF) encode peptides having high homologies with the amino acid sequence of their respective ligands, if the transcription is carried out in 3'-5' direction. Gorcs et al., Peptides, 7: 1137–1145 (1986) report possible recognition of the GnRH receptor by an antiserum against a peptide encoded by nucleotide sequence complementary to mRNA of a GnRH precursor peptide.

GHRH peptides have applications to the fields of animal husbandry, clinical medicine and basic research. For example, it was determined that administration of human GHRH to lactating holstein cows increases the secretion of growth hormone consistently and causes an apparent increase in feed to milk conversion (Enright et al., *J. Dairy Sci.* 69: 344–351, 1986). GHRH peptides are useful in vitro, e.g., as unique research tools for understanding how growth hormone secretion is regulated at the pituitary level and are also be useful in vivo, e.g., to treat symptoms related to growth hormone deficiencies, to increase the rate and extent of growth in commercial animals, to increase milk yield in commercial animals.

SUMMARY OF THE INVENTION

The present invention provides biologically important synthetic peptides and fragments thereof, complementary to GHRH. The present invention also includes antibodies raised against such peptides and methods of using such peptides and antibodies.

One peptide, according to this invention, is complementary in the 3'-5' direction to residues 14–25 of GHRH and has the sequence: H-Asp-Pro-Val-Asn-Ile-Arg-Ala-Phe-Asp-Asp-Val-Leu-Y, wherein Y is OH or NH$_2$ (hereinafter referred to as 3'-5' CP). Another peptide of this invention is complementary in the 5'-3' direction to residues 18–43 of GHRH and has the following sequence: H-Val-Glu-Pro-Gly-Ser-Leu-Phe-Leu-Val-Pro-Leu-Pro-Leu-Leu-Pro-Val-His-Asp-Phe-Val-Gln-Gln-Phe-Ala-Gly-Ile-Y, wherein Y is OH or NH$_2$ (hereinafter referred to as 5'-3' CP).

The GHRH complementary peptides of the present invention or fragments thereof, or antibodies raised against them may be used (1) in vitro, e.g., for various assays, and (2) may be administered in vivo to mammals, including humans, to increase Growth Hormone ("GH") release for therapeutic purposes and for the purpose of increasing growth of poultry and livestock, increasing milk production in cows and possibly increasing wool production in sheep.

BRIEF DESCRIPTION OF THE DRAWINGS

FIG. 1a illustrates the RNA sequence and amino acid sequence of complementary peptides according to the present invention.

FIG. 1b illustrates the homology of complementary peptides of the present invention in the region that corresponds to GHRH (22–27).

DETAILED DESCRIPTION OF THE INVENTION

Figure 2A:
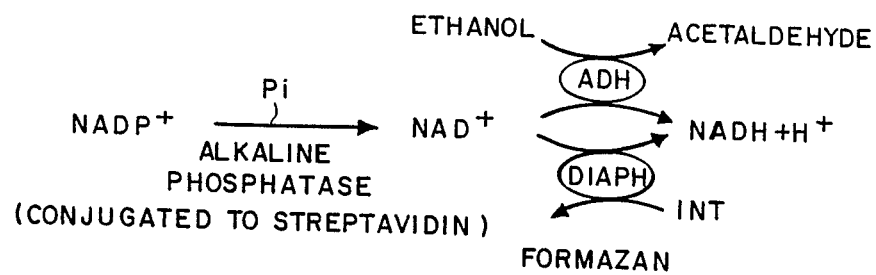
FIG. 2 illustrates the principles of the assays conducted in the examples.

The present invention provides biologically important complementary peptides ("CP") overlapping the sequence of human GHRH (18–25). As mentioned above, Ling et al. found a gradual decrease in relative GH-releasing potency of C-terminal deleted GHRH fragments until reaching hGHRH (1–27) (12% relative potency). A sharp decrease in biological activity was found with shorter fragments, e.g., hGHRH (1–24): 0.02% relative potency; hGHRH (1–19): No activity. Hence, the sequence of hGHRH (20–27) is essential for the receptor ligand interaction. The amino acid sequence of both the 3'-5' CP and 5'-3' CP was derived from the mRNA (Mayo et al., supra) for rat GHRH.

Both the 3'-5' and 5'-3' CP contain a 6 amino acid-long sequence that is identical with a sequence in rat GHRH and human GHRH in hydropathic nature. If one aligns the amino acid sequences of the 3'-5' and 5'-3' CP in antiparallel direction, one can find a high homology in their amino acid distribution in the region that corresponds to GHRH (22–27) (FIG. 1b). The hydrophobic amino acids are the same in both the 3'-5' and 5'-3' CP, while the hydrophilic ones are closely related but have a different charge (Asp vs. Gln). On the contrary, other peptides in the glucagon family have "uncharged" amino acids in position 25 (Trp in gastric inhibitory peptide and glucagon; Gly in secretin, Ser in vasoactive intestinal peptide [VIP] and peptide histi-dine-isoleucine-27 [PHI-27]) and in position 22 (Tyr in VIP and PHI-27).

The peptides of the present invention can be synthesized by any suitable method, such as by exclusively solid-phase techniques, by partial solid-phase techniques, by fragment condensation, by classical solution couplings, or by the employment of recently developed recombinant DNA techniques.

The 12 amino acid long 3'-5' CP of GHRH and the 26 amino acid long 5'-3' CP of GHRH (See FIG. 1a) were synthesized at the Molecular Resource Center, Macromolecular Synthesis Laboratory, University of Tennessee, Memphis, Dr. T. C. Cooper, Director. Applied Biosystems Model 430A, a fully automatic instrument-reagent system for solid phase peptide synthesis, was used. The Model 430A utilized an optimized system based on R. B. Merrifield's concept of solid phase peptide synthesis (Virender et al., *Anal. Biochem.*, 117: 147–157, 1981). Typically, solid phase synthesis occurs from the 'C-' to the 'N-terminal' of the peptide sequence. The alpha-carboxyl group of the C-terminal amino acid residue is covalently attached to an insoluble polystyrene resin bead through an organic linker. The alpha-amino group of this amino acid, and all the other amino acids used in synthesis, are protected by an organic moiety.

A general synthesis cycle consists of: deprotection of the resin-bound alpha-amino group, then washing, neutralization and washing of the resin. Next in the cycle is the formation of a peptide bond between the deprotected alpha-amino group and the activated carboxyl of the next alpha-amino protected amino acid of the sequence. This cycle is repeated until the desired sequence is complete. When synthesis is complete, the peptide is deprotected and cleaved from its polymer support; it is then separated from the resin and purified.

The GHRH binding capacity of both complementary peptides was tested in an ELISA system as described in the examples below. The 3'-5' CP has a GH-stimulating effect as shown in the examples below.

Polyclonal antibodies ("anti 5'-3' CP IgG") were raised in rabbits against the 5'-3' CP and purified using techniques known to those skilled in the art. The 5'-3' CP was coupled to a carrier protein, keyhole limpet hemocyanin (KLH), and used to immunize rabbits. Sera obtained from the rabbits was purified using Protein A affinity-chromatography. Polyclonal antibodies were also raised against the 3'-5' CP and purified using similar techniques.

As shown in the examples below, purified polyclonal anti 5'-3' CP IgG has a GH-stimulating effect. Anti 5'-3' CP IgG stimulates GH secretion from adult male rat pituitaries in cell culture. Thus, interaction of the anti 5'-3' GP IgG preparation and the pituitary cells has a similar effect on GH secretion as the interaction of the GHRH receptor and GHRH.

The 3'-5' and 5'-3' CP, fragments thereof, or analogs thereof having well known substitutions and/or additions, as well as non-toxic salts of any of the foregoing, and antibodies to such peptides, may be used for research purposes or diagnostically, or may be administered therapeutically to mammals, including humans. Antibodies provided by the present invention may be used for preparative procedures, e.g., to purify the GHRH receptor by affinity chromatography.

The 3'-5' CP or 5'-3' CP, fragments thereof, or antibodies against them, ("the active ingredient") can be used for the in vivo treatment of mammalian species by physicians and/or veterinarians. The amount of said active ingredient will, of course, depend upon the severity of the condition being treated, the route of administration chosen and the specific activity of the active ingredient, and ultimately will be decided by the attending physician or veterinarian. Such amount of active ingredient or IgG as determined by the attending physician or veterinarian is also referred to herein as a "treatment effective" amount.

The active ingredient may be administered by any route appropriate to the condition being tested. Preferably, the peptide is injected into the bloodstream of the mammal being treated. It will be readily appreciated by those skilled in the art that the preferred route will vary with the condition being treated.

While it is possible for the active ingredient to be administered as the pure or substantially pure compound, it is preferable to present it as a pharmaceutical formulation or preparation.

The formulations of the present invention, both for veterinary and for human use, comprise the 3'-5' CP or 5'-3' CP, a fragment thereof, analog thereof or antibody thereto, as described above, together with one or more pharmaceutically acceptable carriers therefor and optionally, other therapeutic ingredients. The carriers must be "acceptable" in the sense of being compatible with the other ingredients of the formulation and not deleterious to the recipient thereof. Such carriers are well known to those skilled in the art of pharmacology. Desirably, the formulation should not include oxidation agents and other substances with which peptides are known to be incompatible. The formulations may conveniently be presented in unit dosage form and may be prepared by any of the methods well known in the art of pharmacy. All methods include the step of bringing into association the active ingredient with a carrier which may constitute one or more accessory ingredients. In general, the formulations are prepared by uniformly and intimately bringing into association the active ingredient with liquid carriers or finally divided solid carriers or both, and then, if necessary, shaping the product into the desired formulation.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile. The formulations may be presented in unit or multi-dose containers, for example, sealed ampules or vials.

The invention will be further understood with reference to the following examples which are purely exemplary in nature and are not meant to be utilized to limit the scope of the invention.

EXAMPLE 1

Synthesis of 3'-5' and 5'-3' CP of GHRH Peptides

The syntheses of 3'-5' CP amide, with the sequence: H-Asp-Pro-Val-Asn-Ile-Arg-Ala-Phe-Asp-Asp-Val-Leu-NH$_2$ and 5'-3' CP amide, with the sequence:

H-Ile-Gly-Ala-Phe-Gln-Gln-Val-Phe-Asp-His-Val-
Pro-Leu-Leu-Pro-Leu-Pro-Val-Leu-Phe-Leu-Ser-
Gly-Pro-Glu-Val-NH$_2$ were performed on an Applied Biosystems Model 430A Peptide Synthesizer which is totally microprocessor controlled, utilizing software version 1.2. This machine is a solenoid controlled, gas-driven (prepurified nitrogen or argon) synthesizer. The aminomethyl resin was purchased from Applied Biosystems, Inc. and had an amino acid substitution of about 0.6–0.7 millimoles/gm. of resin. This resin consists of 1% cross-linked polystyrene to which had been attached a phenylacetamidomethyl (PAM) group. The carboxyl terminal amino acid, leucine or isoleucine, in these cases, was attached to the PAM resin and contained an amino terminal blocked with the TBOC (t-butoxylcarbonyl)-protecting group.

After deprotection of this group on the machine utilizing trifluroacetic acid, the peptide was built in a stepwise manner. TBOC-protected amino acids were purchased in pre-weighed amounts (approximately 2 mmoles) in sealed cartridges from Applied Biosystems. The chemical forms of the amino acids used in these peptides are listed below:

| | |
|---|---|
| t-BOC—L—Aspartic acid (O—Benzyl) | t-BOC—L—Glutamine |
| | t-BOC—L—Glutamate (O—BZ) |
| t-BOC—L—Asparagine | t-BOC—L—Glycine |
| t-BOC—L—Alanine | t-BOC—L—Serine (Benzyl) |
| t-BOC—L—Arginine (Tosyl) | t-BOC—L—Histidine (Tos) |
| t-BOC—L—Leucine.H$_2$O | t-BOC—L—Valine |
| t-BOC—L—Isoleucine | |
| t-BOC—L—Phenylalanine | |
| t-BOC—L—Proline | |

O-Benzyl, Benzyl and Tosyl (p-toluenesulfonyl) refer to the type of amino and hydroxyl protecting groups present on the amino acid derivatives.

Briefly, the resin-bound amino acid is deprotected by the addition of trifluroacetic acid, neutralized, and washed extensively. T-BOC protected amino acids are dissolved in suitable solvents and transferred to the activator vessel of the instrument. DCC (Dicyclohexylcarbodiimide) is then added to the dissolved amino acid, and a symmetric anhydride is formed, called a PSA (protected symmetric anhydride). A by-product of the reaction, dicyclohexylurea, forms a precipitate. The equation for this reaction is given below:

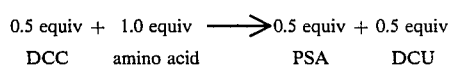

```
0.5 equiv  +  1.0 equiv   ⟶  0.5 equiv  +  0.5 equiv
  DCC        amino acid           PSA           DCU
```

There are three exceptions to the use of amino acid PSA's in the Model 430A cycles; asparagine, glutamine, and arginine are coupled as 1-hydroxybenzotriazole (HOBT) esters. These esters are utilized because symmetric anhydrides of these amino acids are unstable and undergo unacceptable side reactions. In addition to being HOBT-esters, these amino acids are double coupled, that is, two cartridges of these amino acids are required for each cycle. After the initial coupling, the resin is washed, then the coupling is repeated, to increase the yields.

After the PSA is prepared, the amino acid is transferred to the concentrator vessel, where it is purged with nitrogen to remove volatile dichloromethane (DCM). N,N-Dimethylformamide (DMF) is then added to the amino acid. Individual PSA's have varying stabilities in DCM/DMF mixtures, so the temperatures are carefully regulated by the program. HOBT-esters are not purged since they are unstable.

Certain individual amino acids require special treatment. Histidine is one such amino acid. It is purchased as the DCHA (dicyclohexylamine) salt and passed through a suitably prepared AG-50-X8(H+) ion exchange column in DCM just before use. T-BOC-his(-Tos) is unstable in DCM at room temperature, and thus must be placed on the machine within 4 hours of use. Two other alterations in the cycle are required with histidine. Since the amino acid is supplied as a solution, no DCM is delivered to the cartridge, and the purge cycle is shortened to 6.5 minutes because of its instability.

As the amino acids are activated and the solvents are evaporated and changed, the resin is treated with trifluoroacetic acid (TFA) in DCM twice, then washed with DCM to remove some of the TFA. The resin is then neutralized with diisopropylethylamine (DIEA) in DMF and washed with DMF. DMF is the solvent of choice for coupling of activated amino acids to the growing peptide chain.

After the peptide is complete, the T-BOC group is then removed with the standard deprotection step and washed with DCM.

Synopsis of one single couple cycle:

Addition of the first amino acid residue of the first peptide, valine, was carried out in the following manner:

1. The amino acid cartridge was punctured with a needle assembly and approximately 3 ml of dichloromethane (DCM) was delivered to the powdered amino acid. The solution was mixed with nitrogen bubbles for approximately 2 minutes, and the solution transferred to the activator vessel.

2. One millimole of 0.5M dicyclohexylcarbodiimide (DCC) in dichloromethane was delivered to the activator vessel followed by gas purging to mix. The by-product of this reaction, dicyclohexylurea, begins to precipitate almost immediately. After 8 minutes, the solution is filtered through a glass frit, and delivered to the concentrator vessel.

3. During the activation and concentration cycles, the resin, in the reaction vessel, was treated in the following way:

a. 33% trifluoroacetic acid (TFA) in DCM for 2.5 minutes
   b. 50% TFA in DCM for 18 minutes
   c. Three DCM washes
   d. 10% DIEA in DMF for 3 minutes
   e. Five DMF washes The deprotection steps are identical to the above for all amino acids.

4. In the concentrator vessel, the DCM solution was purged with nitrogen gas for a total of about 16 minutes, and approximately 4 ml of DMF was added. The temperature was automatically controlled at 15° C. or below. After the last DMF wash of the resin, the activated amino acid in DMF was delivered to the reaction vessel and coupled for about 25 minutes with vigorous vortexing. Other amino acids utilizing this coupling time are histidine, leucine, isoleucine, phenylalanine and proline. Others such as aspartic acid, glycine, serine and alanine use about 18 minutes. Arginine and asparagine are coupled twice for 42 minutes each.

5. As the peptide chain lengthens, longer coupling times are required and are automatically incorporated into the compiled program as it progresses.

6. After coupling was completed, the resin was drained and washed five times with DCM. Activation of the next amino acid and deprotection of the resin for the next cycle was begun.

Synopsis of a double couple cycle:

1. Two amino acid cartridges were required for the double couple cycles of arginine and asparagine. These were placed one after another in the guideway of the Model 430A synthesizer.

2. The first amino acid cartridge was punctured with a needle assembly and approximately 4 ml of HOBT (1-Hydroxybenzotriazole) in N,N-Dimethylformamide (DMF) (2 mmole) was delivered to the cartridge to dissolve the amino acid. Asparagine requires the addition of 0.3 ml of DCM, and arginine requires 1.5 ml of DCM for complete dissolution. After mixing (6.5 min for asparagine, 8 min for arginine), the solution was transferred to the activator vessel.

3. The HOBT-ester double couple cycles all employ the same transfer process. The HOBT/amino acid mixture is added to 4 ml (2 mmoles) of DCC (dicyclohexylcarbodiimide) in the activator vessel. After precipitation of DCU, the HOBT-ester is transferred to the concentrator vessel after being filtered through a glass frit.

4. The solution is then directly transferred to the reaction vessel, without gas purging.

5. During the previously described activation phase, the resin was deprotected using the following schedule:

a. 33% TFA in DCM for 2.5 minutes
   b. 50% TFA in DCM for 18 minutes
   c. Three DCM washes
   d. 10% DIEA in DMF for 3 minutes
   e. Five DMF washes
   f. Begin first coupling period 6. Coupling then takes place for about 42 minutes with vigorous vortexing. The resin is then washed according to the following schedule:

g. Three DMF washes
   h. 10% DIEA in DMF for 45 seconds
   i. One DMF wash
   j. Three DCM washes 7. The second amino acid cartridge is prepared in the same manner as the first, and coupled for another 42 minutes. The resin is then drained, washed with DMF, then 5 times with DCM.

EXAMPLE 2

ELISA Using 3'-5' and 5'-3'

The principle of the assay is shown in FIG. 2.

Reagents:

Buffers and dilutions

Coating buffer: 41.25 mM $NaHCO_3$/8.75 mM $Na_2CO_3$, pH 9.6, containing 0.1 g/l thimerosal.

Wash buffer No. 1: 12.38 mM $Na_2HPO_4$/2.62 mM $KH_2PO_4$, pH 7.4 containing 135 mM NaCl, 1.0 g/l sodium azide, 5000 USP units/l heparin and 0.5 ml/l Tween.

Diluting buffer No. 1: Wash buffer No. 1 containing 1% (w/v) BSA and 1% (v/v) normal goat serum (NGS).

Wash buffer No. 2: 10.0 mM TRIS/HCl buffer (pH 7.4) containing 135 mM NaCl, 1.0 g/l sodium azide, 5000 USP units heparin and 0.5 ml/l Tween 20.

Diluting buffer No. 2: Wash buffer No. 2 containing 1% (w/v) BSA.

Substrate buffer: 50 mM diethanolamine, 0.5 mM $MgCl_2$, 0.1 mM $ZnCl_2$, 1.0 g/l sodium azide, 10N HCl to adjust the pH to 9.5.

Amplifier buffer: 16.5 mM Na$_2$HPO$_4$, 3.5 mM KH$_2$PO$_4$, 1.0 g/l sodium azide, pH 7.2.

Substrate: 0.1 mM β-NADP dissolved in substrate buffer.

Stock solutions of enzymes: Alcohol dehydrogenase (ADH, Sigma, A-3263) and diaphorase (Sigma, D-2381) were dissolved in H$_2$O in a concentration of 20 and 15 mg/ml, respectively. Aliquots were stored frozen at −70° C.

Amplifier: 96 ml amplifier buffer, 4 ml absolute ethanol, 0.5 g BSA, 28 mg para-iodo-nitrotetrazolium violet (INT, Sigma I-8377). After the INT had been dissolved, 200 µl of ADH and 200 µl of diaphorase solution was added to 20 ml solution immediately before use.

All materials used for coating of microELISA plates (Immunolon-2, Dynatech), were dissolved in coating buffer.

All other reagents were diluted with diluting buffer No. 1 with the exception of the streptavidin-alkaline phosphatase conjugate (SA-AP, Bethesda Research Laboratories) which was diluted in diluting buffer No. 2.

Antisera. Rat GHRH antiserum (rabbit) was purchased from Peninsula Laboratories, Inc., Belmont, Calif. (Lot. No. 008769). This antibody has no cross-reactivity with human pancreatic GHRH (hpGHRH) (1-44) NH$_2$, hpGHRH (1-40), porcine GHRH, PHI-27 and VIP. The lyophilized powder was rehydrated in distilled water; further dilutions were made with buffer. Antirabbit IgG (goat) was purchased from Sigma (Cat. No. R-4626).

Biotin-labeling of anti-rabbit IgG. Five mg of the anti-rabbit IgG (goat) (GARGG) was dissolved in 5 ml freshly prepared, preservative-free 0.1M sodium bicarbonate solution (pH 8.4); 5 mg N-hydroxy-succinimidobiotin (NHSB, Sigma H-1759) was dissolved in 1.0 ml dimethyl sulfoxide (DMSO). One ml of NHSB/DMSO solution was added to 5 ml GARGG. The compounds were incubated for 4 hrs at room temperature (RT), then the solution was dialyzed against 2×1..0 l PBS (pH 7.4, containing 0.1% sodium azide) for 24 hrs each, at 4° C. Finally the biotin-labelled GARGG (bio-GARGG) was aliquoted and stored frozen at −70° C. until used.

Detection system. The detection system (FIG. 2a) is based on Self's enzyme amplification method (Self, 1985; Johansson, Stanley and Self, 1985; Johansson, Ellis, Bates, Plumb and Stanley, 1986). This method allows measurement of $43.10^{-20}$ ml thyroid stimulating hormone (TSH)/well; thus, it exceeds the theoretical sensitivity ($10^{-14}$M) of the iodine-125 detection system (Johansson, Ellis, Bates, Plumb and Stanley, 1986; Jackson and Ekins, 1986). Avidin has an extremely high affinity to biotin (dissociation constant $10^{-15}$M) and is a useful tool in ELISA systems (Guesdon, Ternynck and Avrameas, 1979; Vilja, Krohn and Tuohimaa, 1985).

Figure 2B:
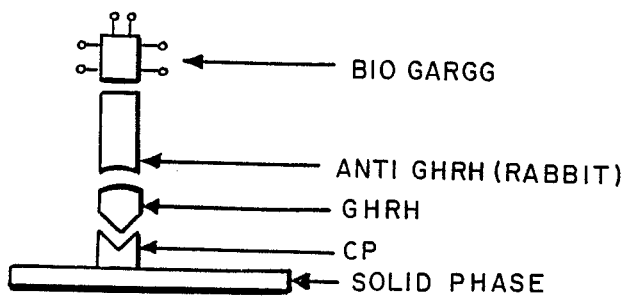

FIG. 2b depicts a solid-phase immunoassay in which a CP is bound to the solid phase and the antibody binds to GHRH, when GHRH forms a GHRH-CP complex, i.e., where the CP binds at a different site from the antibody.

Figure 2C:
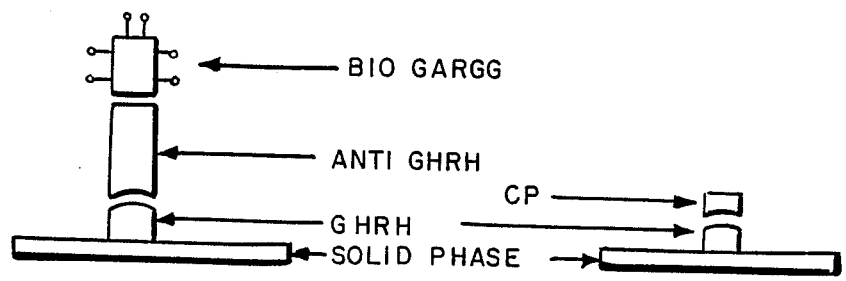

FIG. 2c depicts a solid-phase immunoassay where GHRH is bound to the solid phase and the antibody and the CP bind GHRH at the same site; thus the binding can be shown as a competition between the antibody and the CP for the binding site of GHRH. To exclude (or at least reduce) the non-specific binding between the peptides and/or the proteins based on electrostatic charge differences, 5 USP units/ml sodium heparin was added to the buffers (Pesce, Apple, Sawtell and Michael, 1986).

The ELISA was carried out as follows:

Enzyme-linked Immunoassay:

1. Coating. Materials (e.g., CP's) were dissolved at the concentrations indicated in the figures in coating buffer. 120 µl/well, 4° C., 16 hrs.
2. Wash: 3×200 µl wash buffer No. 1.
3. Block for non-specific binding: diluting buffer No. 1, 150 µl/well, 37° C., 1 hr.
4. Wash: 1×200 µl wash buffer No. 1.
5. GHRH in diluting buffer No. 1, 110 µl/well, 37° C., 1 hr. (FIG. 2b).
6. Wash: 4×200 µl wash buffer No. 1.
7. Anti-GHRH serum diluted in diluting buffer No. 1, 110 µl/well, 37° C., 1 hr.
8. Wash: 4×200 µl wash buffer No. 1.
9. Bio-GARGG, 110 µl/well, 37° C., 1 hr.
10. Wash: 4×200 µl wash No. 2.
11. SA-AP in diluting buffer No. 2, 100 µ/well, 37° C., 1 hr.
12. Wash: 6×200 µl wash buffer No. 2.
13. Substrate: 120 µl/well, RT, 30 min.
14. Amplifier: 190 µl/well, RT, 30 min.
15. Stop the reaction by 25 µl/well 1.0N HCl.
16. Double wavelength spectrophotometry. Specific absorption at 492 nm.

When the wells were coated by GHRH, steps 5-6 were omitted, and the anti-GHRH serum was coincubated with CPs.

Figure 3:
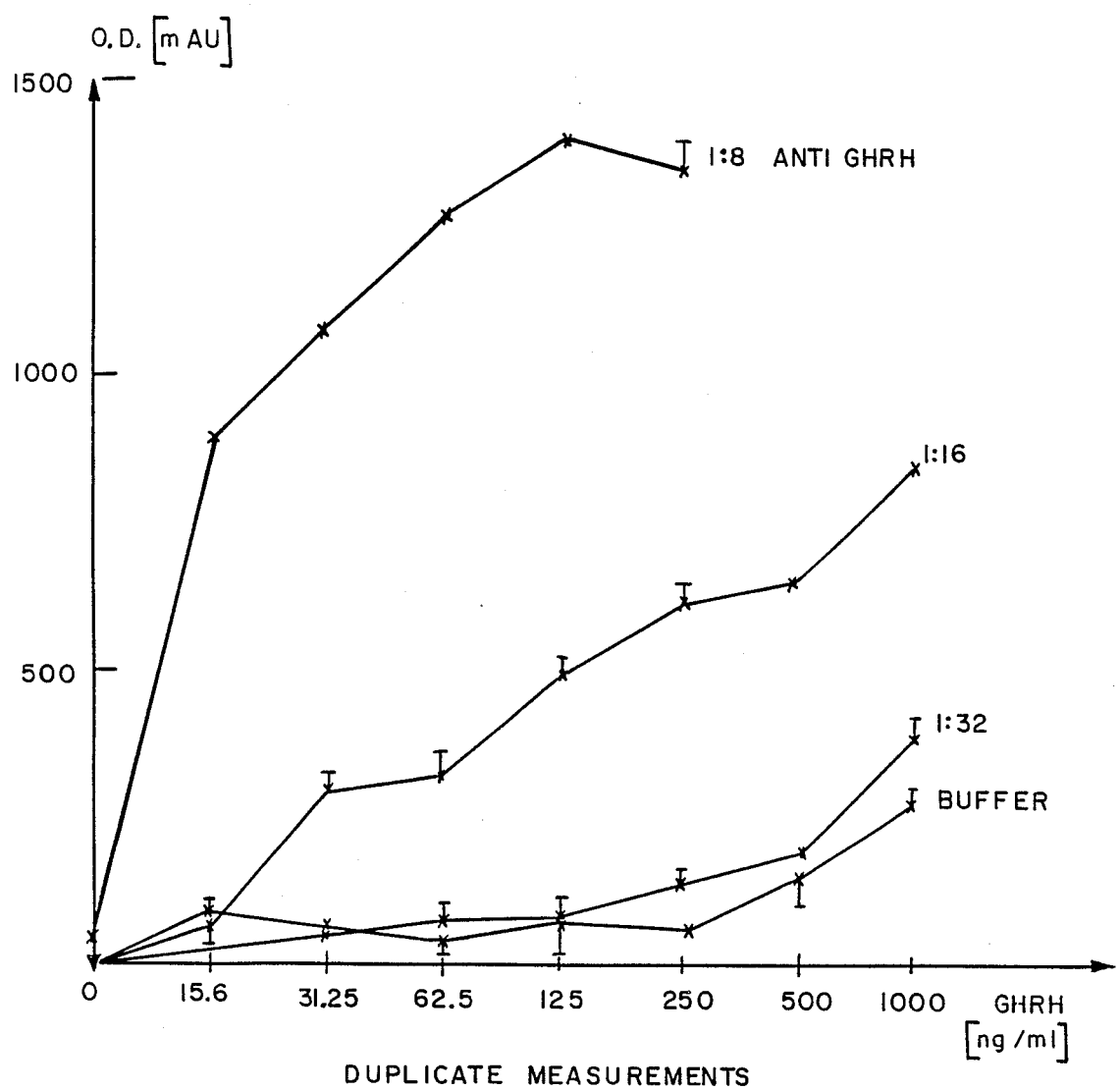
FIG. 3 illustrates the determination of optimum dilutions of GHRH and anti-GHRH in Example 2.1, below.

2.1: Determination of optimum dilutions of GHRH and anti-GHRH. The plate was coated with a dilution series of GHRH (range: 15.6–1000 ng/ml). The dilution of the antiserum recommended for RIA by Peninsula was considered 1:1. Each concentration of GHRH was detected by a dilution series of antiGHRH (range: 1:2–1:32). The results are plotted in FIG. 3. Dilutions of antiGHRH 1:2 and 1:4 gave a high optical density that exceeded the range of the ELISA-reader. Similarly, at the dilution of 1:8, 0.5 and 1.0 µg/ml GHRH resulted in extremely high optical density.

Figure 4:
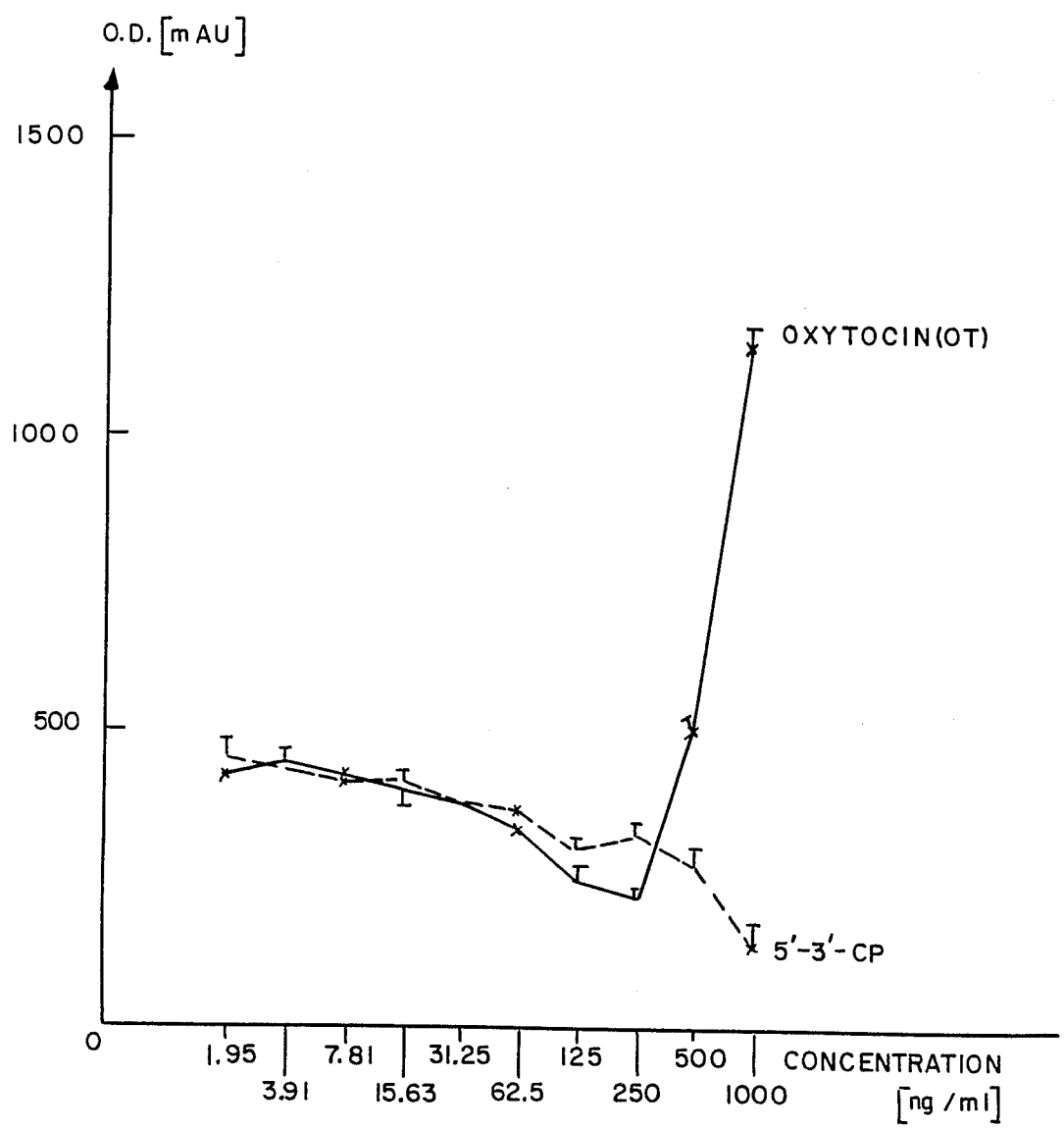
FIG. 4 illustrates the results of the binding study in Example 2.2., below.

2.2: Binding studies according to FIG. 2b. The plate was coated with increasing amount of 5'-3' CP or oxytocin (OT) as a control peptide, as indicated in FIG. 4. There was a clearcut decreasing tendency in optical density as the concentration of the peptides was increased. If there is a binding between the 5'-3' CP and GHRH, and the bound GHRH is capable of binding the antibody, there should be an increase in the optical density as the concentration of 5'-3' CP was increased (GHRH concentration and the antiGHRH dilution were constant: 31.25 ng/ml and 1:8, respectively). However, we found the contrary. On the other hand, oxytocin (OT) at extremely high concentrations could bind GHRH. We consider this interaction non-specific; thus, OT had higher non-specific binding to GHRH than 5'-3' CP. The lack of increase in optical density in the case of 5'-3' could be for two different reasons: (1) there is no GHRH-binding capacity at all; (2) 5'-3' CP and the anti-GHRH antibody bind GHRH at the same site. Experiment 2.3 was designed to answer this question.

The same experiment was carried out for the 3'-5' CP using the same (w/v) concentrations. Again, there was no increase in the optical density (data not shown).

Figure 5:
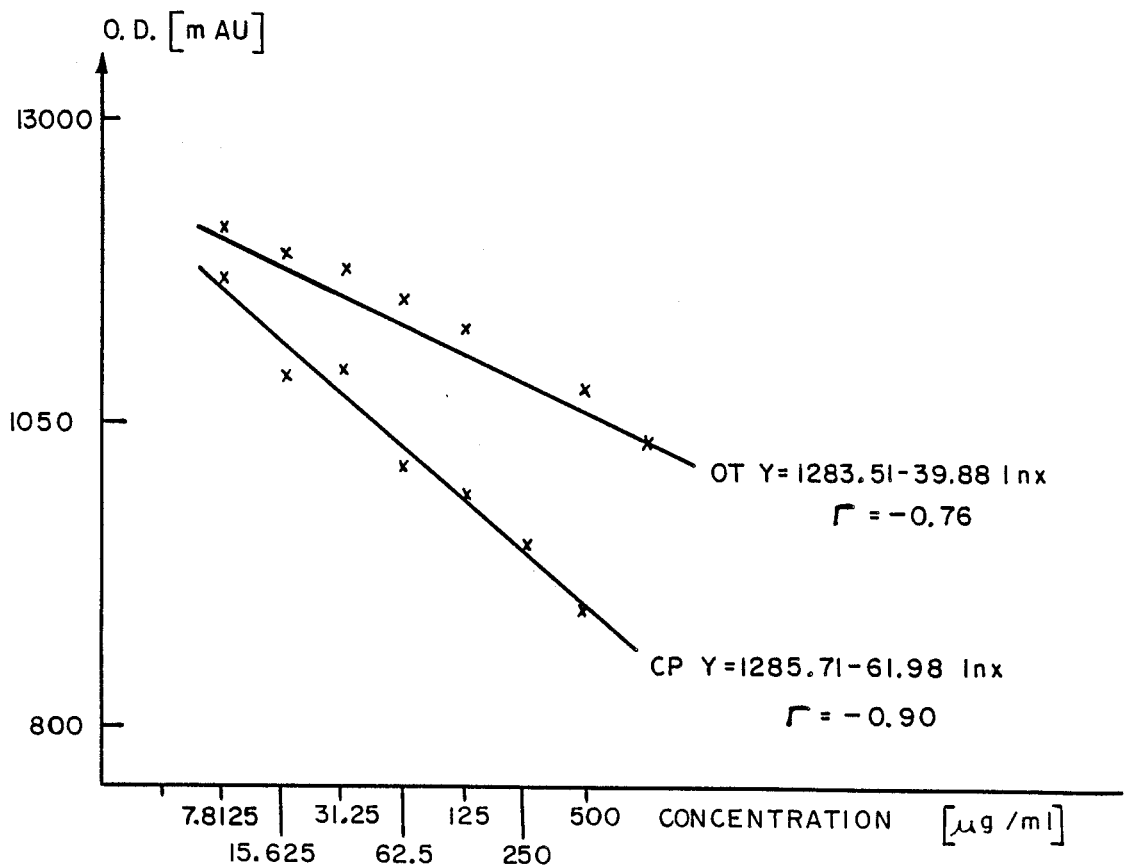
FIG. 5 illustrates the competition between rabbit anti-GHRH anti-serum and 5'-3' CP or oxytocin for solid phase GHRH.

2.3: Binding studies according to FIG. 2c. The plate was coated with 62.5 ng/ml GHRH. 5'-3' CP was coincubated with an equal volume of 1:4 antiGHRH serum; thus, the final dilution of the antibody was 1:8. Final concentrations of the peptide are indicated in FIG. 5. OT (a peptide having non-specific binding activity for GHRH) was used as control. Both OT and 5'-3' CP could displace the antibody from GHRH binding, however, CP had a significantly higher potency than OT. The difference in the slopes of the displacement curves probably represents specific binding between 5'-3' CP and GHRH, or the antibody might have cross-reactivity with the complementary peptide. However, the latter is excluded by the results of Experiment 2.2.

EXAMPLE 3

Immunization of Rabbits with the 5'-3' CP 3.1 Coupling of the peptide to carrier protein. 1.2 mg keyhole limpet hemocyanin (KLH, Sigma H-2133) was dissolved in 15 mM $KH_2PO_4/Na_2HPO_4$ PBS, pH 7.2. The solution was centrifuged, and the supernatant was used to dissolve 3 mg 5'-3' CP. While constantly stirring, 1.5 ml 20 mM glutaraldehyde (E.M. grade, Polysciences cat #1909) was added dropwise to the peptide solution and incubated at room temperature for 60 min. The reaction product was dialyzed against $2 \times 2$ 1 of PBS at 4° C. The final volume was divided into 5 equal aliquots and kept frozen at −20° C. until further use.

3.2 Immunization protocol. The rabbits were bled before the beginning of the immunization to obtain pre-immune sera for control experiments. For the initial injection, two aliquots were emulsified in three volumes of complete Freund's adjuvant. The emulsion was injected subcutaneously into three albino Myrtle's rabbits in equal doses, 0.1 ml/injection site. Three boosters were given subcutaneously at 10-day intervals using incomplete Freund's adjuvant, 0.1 ml/injection site.

Twenty-four days after the initial exposure, the rabbits were bled from the auricular vein twice a week. Thirty-fifty ml of blood was collected each time. The samples were allowed to clot overnight at 4° C., then centrifuged at 2000 rpm for 30 min. The sera were harvested and kept frozen in aliquots at −70° C. until further use.

3.3 Evaluation of the immune response. The antibody production was monitored using enzyme-linked immunosorbent assay (ELISA). Dynatech Immulon-1 micro-ELISA plates were coated with various concentrations of the 5'-3' CP or with coating buffer as control. The solid phase peptide was exposed to various dilutions of the antiserum obtained from a rabbit 45 days after the beginning of the immunization. The IgG bound to the solid phase was detected with biolinylated goat anti-rabbit gamma globulin (bioGARGG) and streptevidin-alkaline phosphatase conjugate. The $\beta$-NADP+ substrate and the alcohol dehydrogenase/diaphorase enzyme amplification technique was used, which converts the p-iodonitrotetrazolium violet to formazan. The color end product was read at 490-405 nM (dual wavelength) using the Bio-Tek EL 310 automatic EIA-reader.

Figure 6:
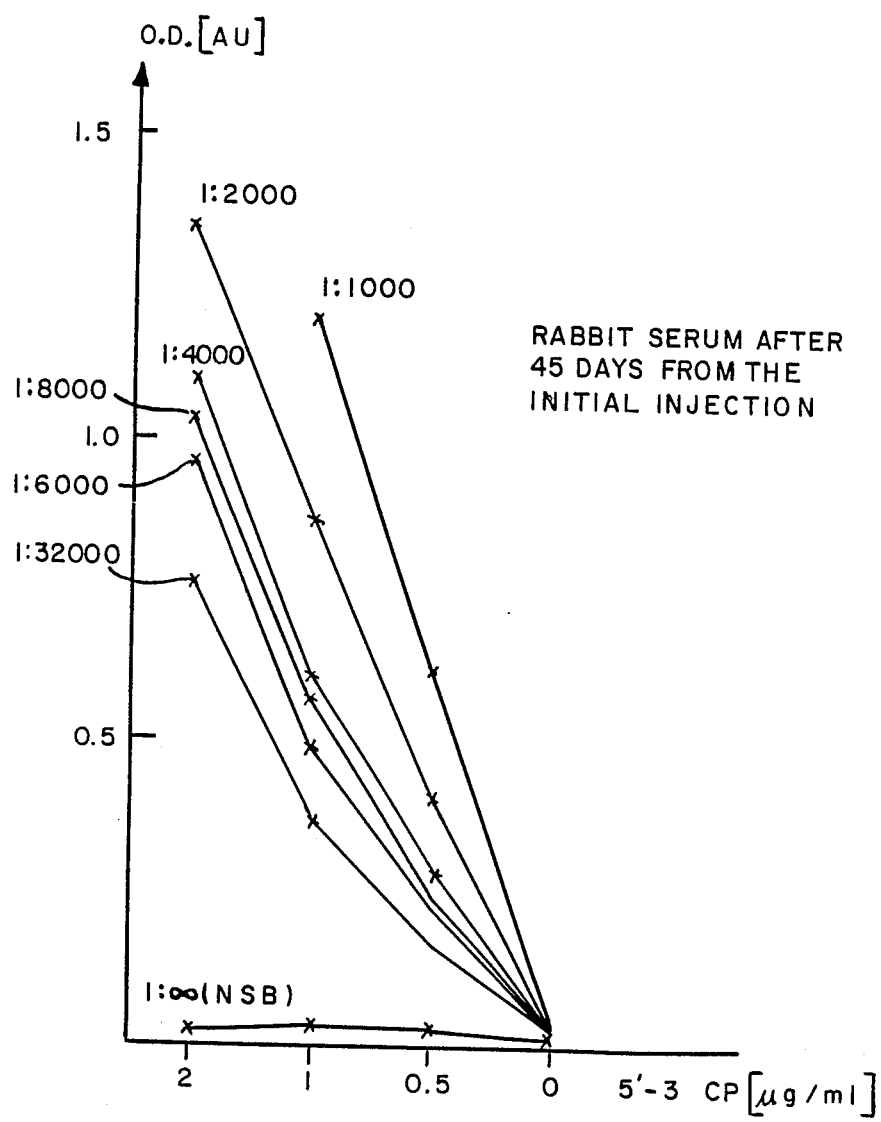
FIG. 6 illustrates the interaction between rabbit antiserum and solid phase 5'-3' CP on Dynatec Immulon-1 plate.

3.4 Immunization of the rabbits with 5'-3' CP. FIG. 6 demonstrates that the rabbit serum contains high titer antibodies against the 5'-3' CP. Based on this experiment, we chose 1.0 μg/ml 5'-3' CP for coating to monitor the timecourse of the immune response. This experiment was then repeated using various dilutions of the sera obtained throughout the immunization process in order to establish the time course of the immune response. Dilutions of the pre-immune serum and the "infinite dilution" (diluting buffer without serum) were used as control.

During the immunization, it came to our attention that the rabbits which produced high titer antibodies to the 5'-3' CP grew larger than the others.

|  | Rabbit No. | | | | | |
| --- | --- | --- | --- | --- | --- | --- |
|  | 1 | 2 | 3 | 4 | 5 | 6 |
| Peptide | 3'-5'CP | 3'-5'CP | 3'-5'CP | 5'-3'CP | 5'-3'CP | 5'-3'CP |
| BW[g] | 5262 | 5700 | 5070 | 6260 | (died) | 5445 |

Figure 7:
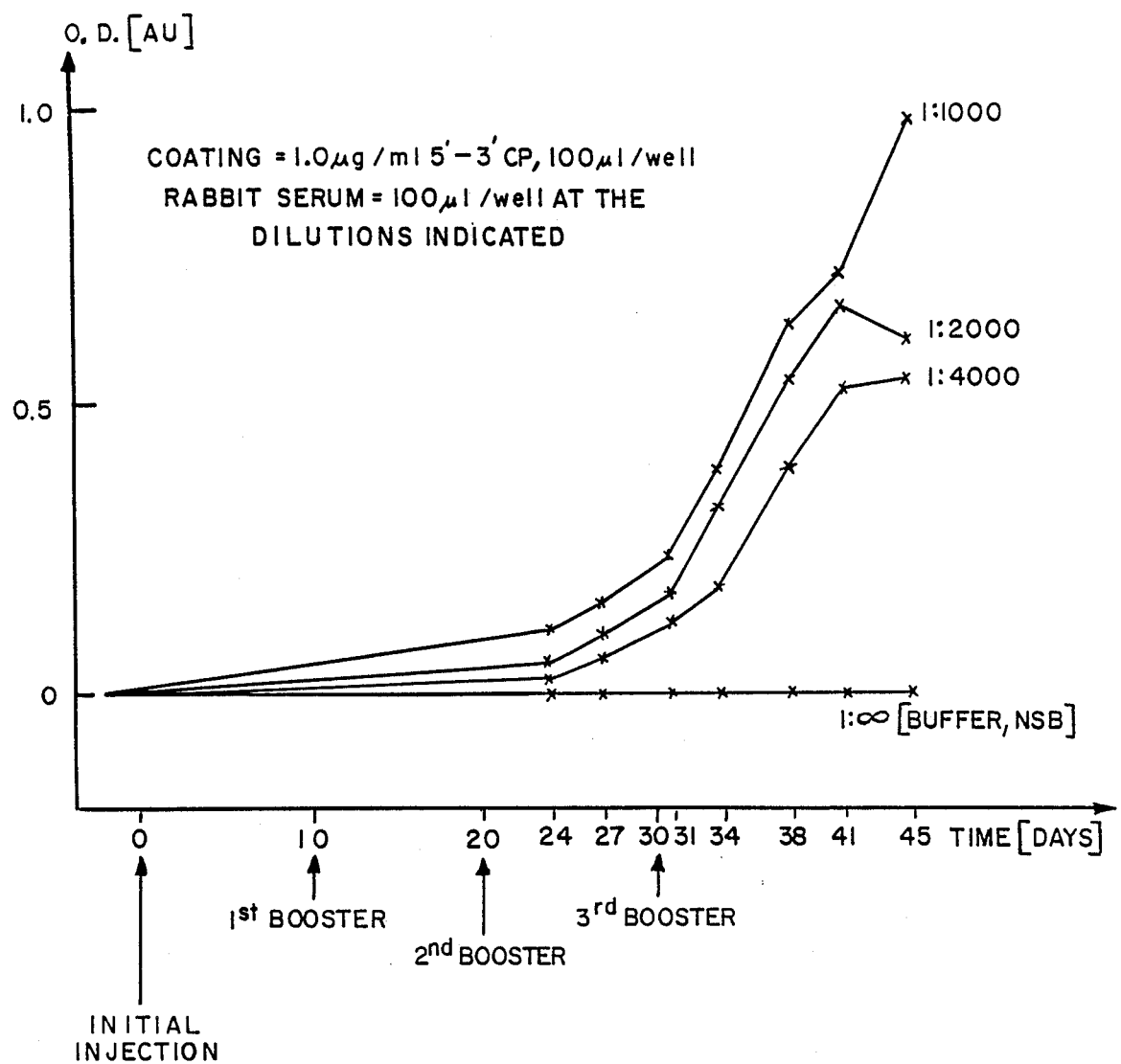
FIG. 7 illustrates the time course of the immune response in rabbits after being injected with the 5'-3' CP.

As shown in FIG. 7, the pre-immune serum did not bind to the solid phase 5'-3' CP even in the highest concentration used. Anti5'-3' CP antibodies gradually appeared in the serum during the immunization protocol, and the binding was related to the dilution.

The antiserum showed very low cross-reactivity with GHRH, LHRH, glucagon or 3'-5' CP (data not shown); thus, it is specific for the antigen (5'-3' CP).

EXAMPLE 4

Purification of the IgG Fraction from Rabbit Sera 4.1 Purification of IgG fraction. The IgG fraction was purified from the pre-immune serum and the immune serum of the rabbit that grew the largest (Rabbit 4, Example 3 above).

4.2 Coupling of Protein A to Affi-Gel 10 beads. Ten ml of Affi-Gel 10 (BIO-RAD) was washed in $3 \times 30$ ml anhydrous isopropanol, then in $3 \times 30$ ml ice-cold distilled water.

5 ml Protein A (Sigma P-6650) was dissolved in 1.0 ml coupling buffer (0.1M $NaHCO_3$, pH 8.2, 4° C.) and added to 2 ml Affi-gel in the same buffer. The mixture was shaken overnight at 4° C., then the remaining binding sites were blocked with 200 μl 1.0M ethanolamine hydrochloride (pH 8.0), 2 hrs at 4° C. with constant shaking. The column was packed in a BIO-RAD Econo-Column (ID-1.0 cm, length=5 cm), then washed extensively with 0.1M $NaHCO_3$ (pH 8.0). Finally the column was washed with PBS containing 0.1% $NaN_3$ and kept at 4° C. until further use.

4.3 Coupling of KLH to Affi-Gel 10 beads. The procedure was basically the same as above. Fifteen mg KLH was dissolved in 10 ml coupling buffer and added to 4 ml Affi-Gel 10. The remaining binding sites were blocked with 0.4 ml 1.0M ethanolamine HCl.

4.4 Affinity-chromatography. One ml of the pre-immune serum was diluted with 1.0 ml PBS. The diluted serum was passed through the Protein A column ten times, then the column was washed extensively with PBS. Twenty drop fractions were collected, and the protein concentration was monitored with UV-spectrophotometry using a Beckman DU-40 instrument. Rabbit gamma globulin (Sigma G-0261) was used for calibration. The absorption spectrum was scanned, and the peak appeared at $\lambda = 290$ nm. When the UV-absorption of the fractions reached the background level, the column was washed further with PBS for several fractions, then the buffer was switched to 0.1M citrate buffer (50 mM citric acid, 50 mM $Na_2HPO_4$, pH 3.6), and the protein-A bound IgG was eluted. The fractions were collected until the absorbance reached the background, then the fractions containing significant amounts of IgG were pooled and dialyzed against PBS at 4° C. overnight.

The column was washed with excess citrate buffer and PBS, then the anti-serum obtained after 45 days from the beginning of the immunization was purified the same way.

After completing the dialysis, the pre-immune IgG was passed through the KLH column 5 times, then the column was washed with PBS. The IgG-containing fractions were collected and pooled. Then the column was washed with citrate buffer, but no significant amount of protein was eluted.

In the next step, the IgG obtained from the immuneserum was passed through the KLH column five times, PBS fractions were collected, and all these IgG fractions were pooled. Then a large amount of IgG was eluted from the column with 0.1 citrate buffer (pH 3.6), and further with 0.1M citric acid (pH 2.2). The acidic IgG fractions were dialyzed against PBS.

Figure 8:
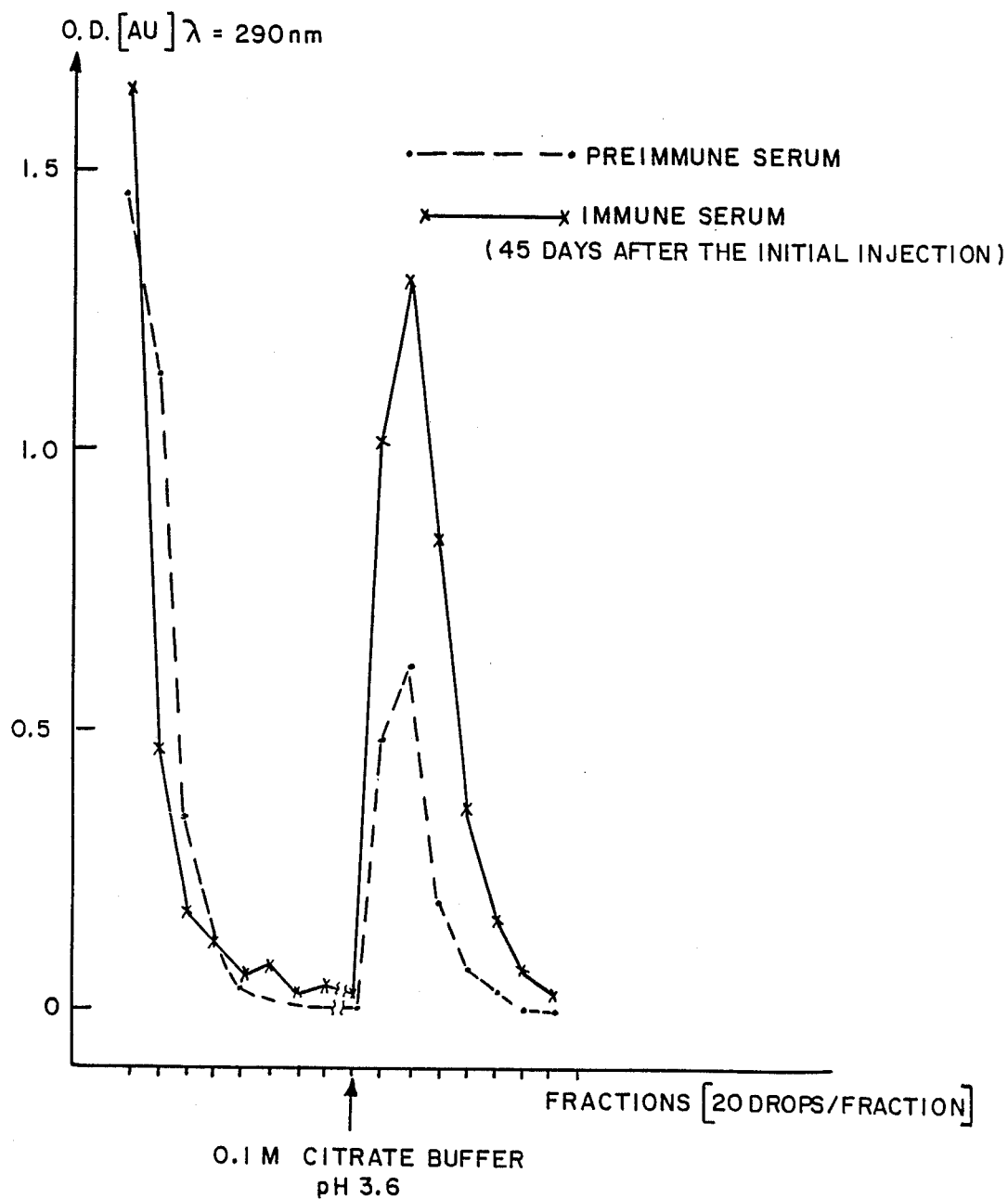
FIG. 8 illustrates Protein A affinity chromotography of pre-immune serum and immune serum.

FIG. 8 demonstrates that the non-IgG protein levels were similar before and after the immunization, while the IgG fraction was substantially higher in the immune serum.

4.5 Testing the purified IgG molecules. Nunc-Immuno Plate I F was coated with 1.0 µg/ml 5'-3' CP or 1.0 µg/ml KLH, 100 µl/well, 4° C., 16 hr. The wells were washed 5 times, then the non-specific binding sites were blocked. Anti 5'-3' CP or antiKLH IgG molecules were added at various concentrations to the wells, then the reaction was evaluated as described above. As the Nunc plate has substantially higher protein-binding capacity then the Dynatech Immulon-1 plate, the reaction became so intensive that the optical density exceeded the range of the reader. Thus, 100 µl reaction product was transferred from each well to another plate and diluted with 100 µl distilled water. The absorbances are plotted in FIG. 9.

Figure 9:
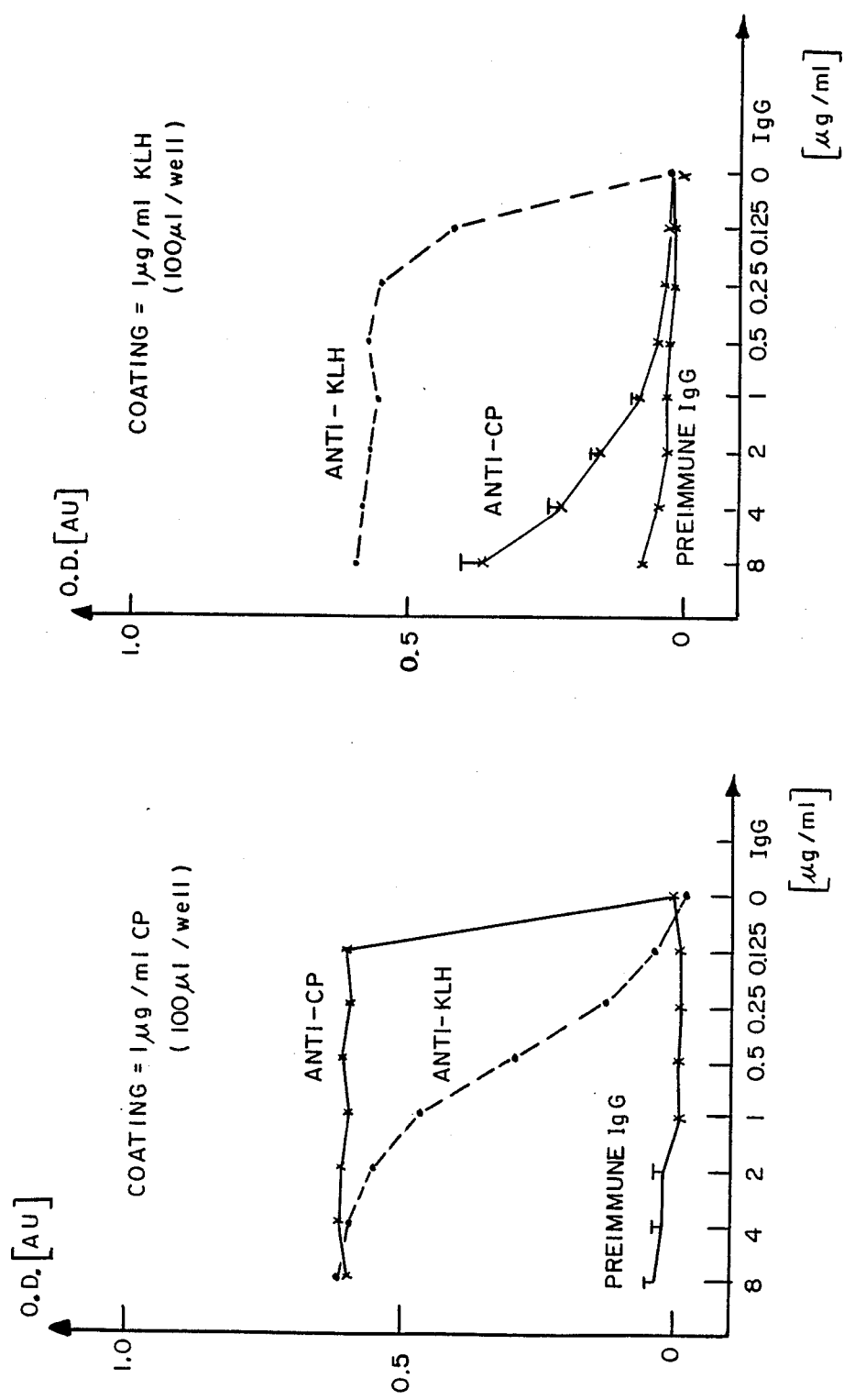
FIG. 9 illustrates the specificity and dose-response of purified 5'-3' CP IgG.

As indicated in FIG. 9, the pre-immune IgG had no significant binding capacity to either the 5'-3' CP or KLH. The anti 5'-3' CP IgG was bound equally to the solid phase 5'-3' CP throughout the whole dilution range tested, hence it obviously has high affinity to the antigen. The antiKLH IgG also exhibited binding to the 5'-3' CP, though the affinity was significantly lower. The anti 5'-3' CP IgG fraction demonstrated a moderate, but significant binding to the KLH, while the antiKLH IgG showed higher binding capacity to its antigen.

EXAMPLE 5

Effect on GH Secretion in vitro 5.1 Preparation and culture of pituitary cells. Pituitary glands were collected from adult male Holtzman rats in Medium 199 (M199) with 3 g/l BSA, 10 mM HEPES (pH 7.4), penicillin (100 U/ml) and streptomycin (0.1 g/l). The tissue was minced and digested with 0.5% solution of the 1:250 Trypsin (Difco) followed by DNAase treatment according to the procedure of Loumaye & Catt (1983). The cell yield was ca. $1.3 \times 10^6$ cells/gland. The viability as determined by trypan blue exclusion was over 95%. The cells were cultured in Falcon 24-well plates of a density of $2.5 \times 10^5$ cells/well in 500 µl M199 containing 5% fetal calf serum, 5 nM dexamethasone, 10 mM HEPES, 100 U/ml penicillin, 0.1 g/l streptomycin at 37° C. in humidified 95% $O_2$/5% $CO_2$. After 4 days of culture, the cells were washed twice with M199 containing 0.3% BSA 5 mM dexamethasone, 10 mM HEPES (pH 7.4), penicillin (100 U/ml) and streptomycin (0.1 g/9) and were incubated with the same culture medium to obtain basal secretion rate, or with growth hormone releasing hormone (GHRH, 5'-3' CP, 3'-5' CP, anti 5'-3' CP IgG or combination of GHRH and anti 5'-3' IgG), at various concentrations for 18 hrs at 37° C. in 95% $O_2$/5% $CO_2$. Each treatment was carried out in triplicate. The culture media from each well were collected at the end of the incubation and stored frozen until assayed for GH by RIA.

5.2 Growth Hormone Radioimmunoassay (GH RIA). In the GH RIA, the NIADDK rat GH kit was used. GH was labelled with $^{125}I$ using the chloramine-T method, and the tracer was purified on Sephadex G-75 column. 16,000 cpm tracer in 100 µl volume was added to each tube. The final dilution of the antibody was 1:30,000, resulting in about 50% specific binding. The detection limit was <25 pg/tube. Precipitation was obtained with IgG-sorb (The Enzyme Center, Inc.).

Figure 10:
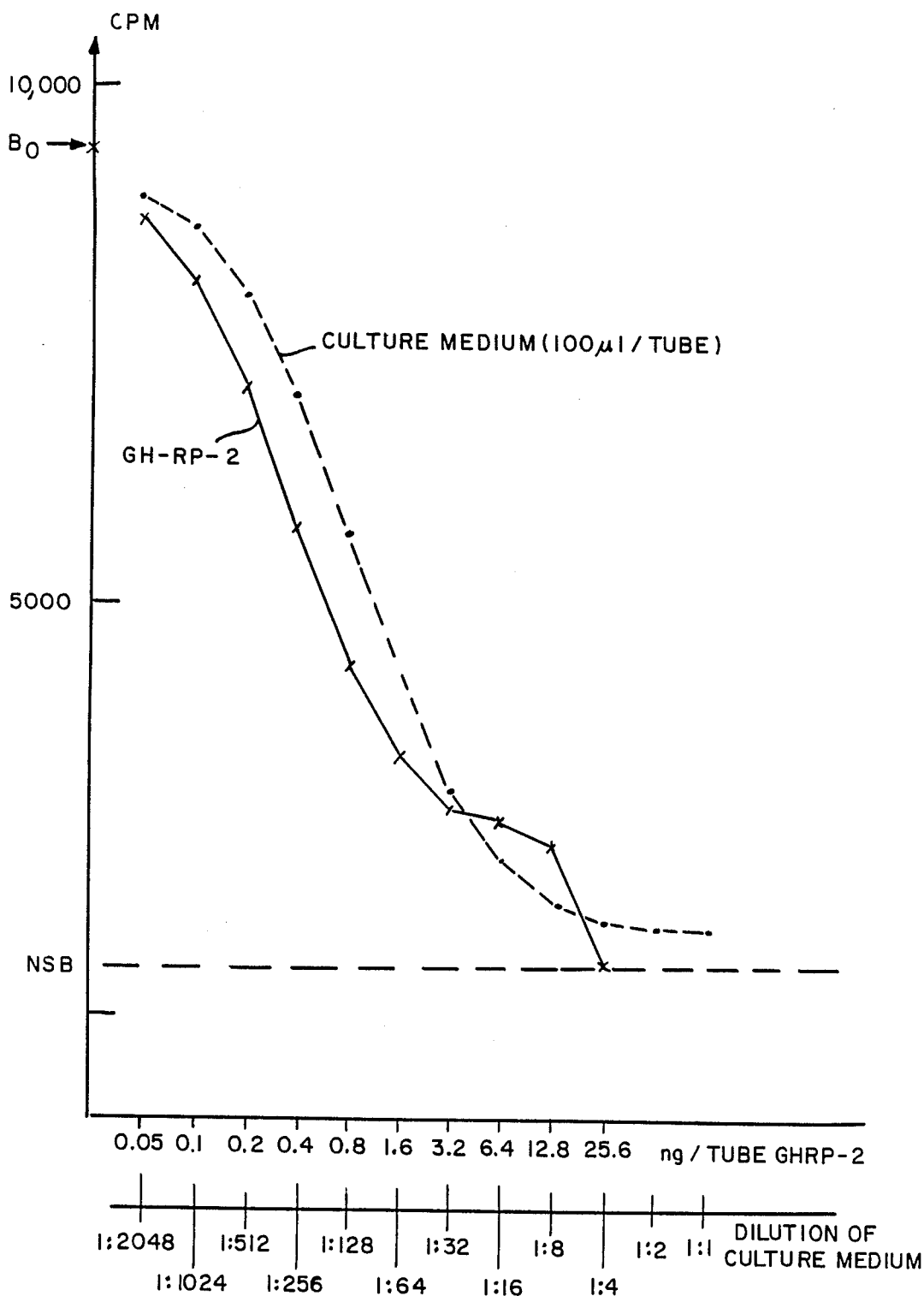
FIG. 10 illustrates the parallelism between the displacement curves of GH RP-2 and in vitro secreted GH.

5.3 GH secretion in vitro: effect of various compounds. A small aliquot was pooled from each control culture to establish the parallelism in the displacement between a standard reference preparation of GH (GH RP-2), courtesy of Dr. A. F. Parlow, NIADDK, NIH, and the culture media containing GH secreted in vitro as obtained in paragraph 5.1 above. Based on this experiment, we determined the dilution needed to measure GH levels, and we chose that part of the displacement curve, where the parallelism was the best. See FIG. 10.

Figure 11:
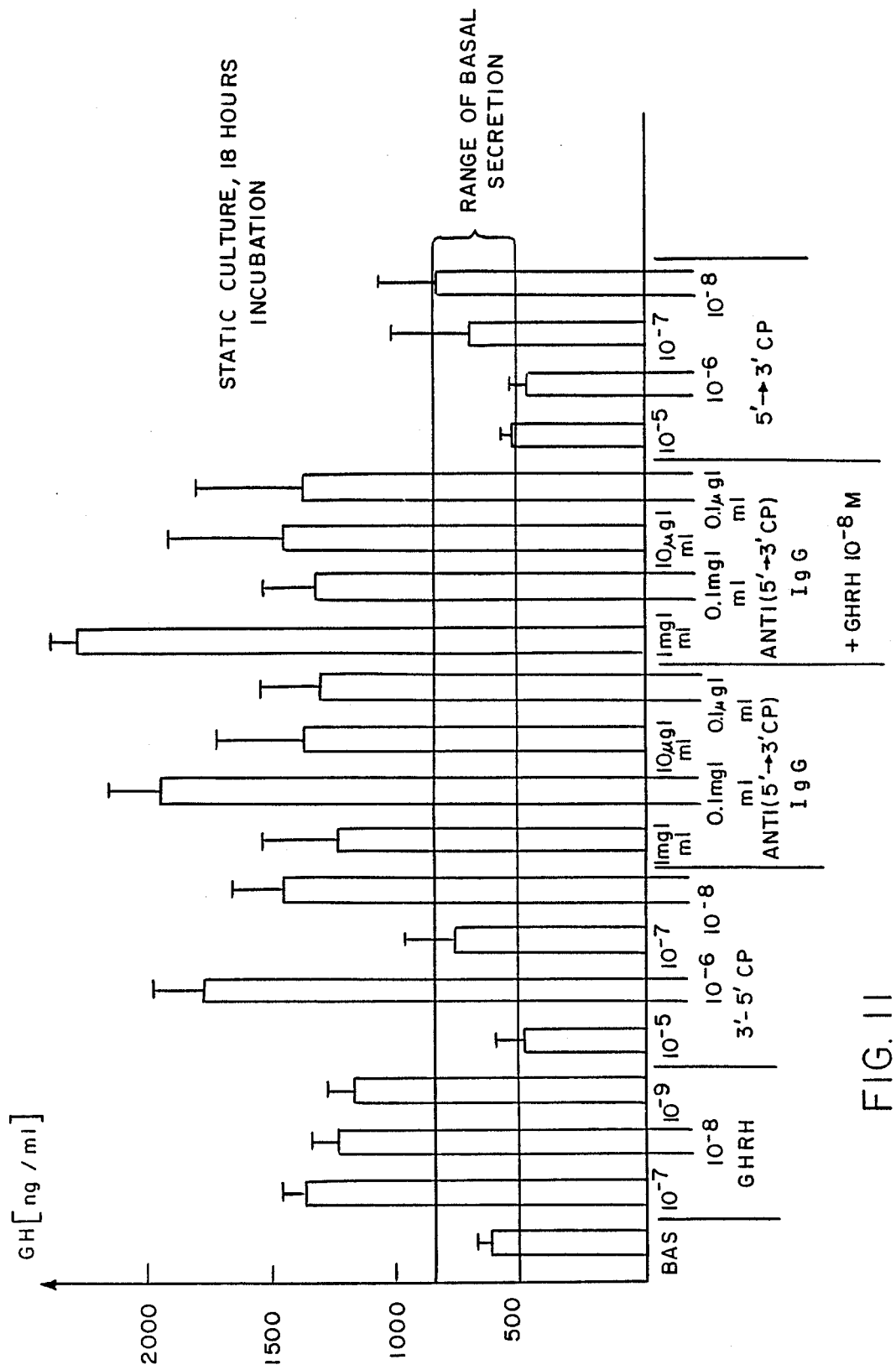
FIG. 11 illustrates the effect of different compounds on GH secretion in vitro.

The baseline secretion was established in five triplicates assigned between the treatment wells. Each treatment was carried out in triplicate. See FIG. 11. GHRH stimulated GH secretion in all doses studied ($10^{-9}$–$10^{-7}$M). The 3'-5' CP had no effect at the doses of $10^{-5}$ and $10^7$, but markedly stimulated GH secretion at the doses of $10^{-6}$ and $10^{-8}$M. The 5'-3' CP itself had no substantial effect on GH secretion ($10^{-8}$–$10^{-5}$M). On the other hand, the anti 5'-3' CP IgG demonstrated GH increasing activity in all doses studied (0.1 µg/ml-1.0 mg/ml). This stimulating activity is not attributed to the salts being present in the IgG preparation, since the lyophilized IgG was diluted and dialyzed against the culture medium before use. The 0.1 µg/ml dose of the IgG preparation contains less than $10^{-9}$M IgG, hence its action is based on high-affinity binding. Co-incubation of the IgG with $10^{-8}$ GHRH was synergistic only at the highest dose used (1.0 mg/ml IgG).

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A synthetic peptide having the formula:

H-Asp-Pro-Val-Asn-Ile-Arg-Ala-Phe-Asp-Asp-Val-Leu-Y wherein Y is OH or $NH_2$ or a non-toxic salt thereof.

2. A method of stimulating the release of growth hormone in a mammal, the method comprising administering to the mammal an effectve amount of a peptide in accordance with claim 1.

3. A method of increasing milk production in a mammal, the method comprising administering to the mammal an effective amount of a peptide in accordance with claim 1.

4. A method of accelerating the growth of a mammal, the method comprising administering to the mammal an effective amount of a peptide in accordance with claim 1.

5. A synthetic peptide having the formula:

H-Val-Glu-Pro-Gly-Ser-Leu-Phe-Leu-Val-Pro-Leu-Pro-Leu-Leu-Pro-Val-His-Asp-Phe-Val-Gln-Gln-Phe-Ala-Gly-Ile-Y wherein Y is OH or $NH_2$ or a non-toxic salt thereof.

* * * * *